United States Patent [19]

Dietrich et al.

[11] 4,454,362
[45] Jun. 12, 1984

[54] PROCESS FOR PRODUCING PENTACHLORONITROBENZENE

[75] Inventors: Robert F. Dietrich, Clinton; Walter A. Gay, Cheshire, both of Conn.

[73] Assignee: Uniroyal, Inc., New York, N.Y.

[21] Appl. No.: 444,757

[22] Filed: Nov. 26, 1982

[51] Int. Cl.³ ............................................. C07C 79/10
[52] U.S. Cl. .................................................... 568/938
[58] Field of Search ......................................... 568/938

[56] References Cited

U.S. PATENT DOCUMENTS

| | | | |
|---|---|---|---|
| 3,026,358 | 3/1962 | Lojewski | 568/938 |
| 3,984,487 | 10/1976 | Watts et al. | 568/938 |
| 4,026,955 | 5/1977 | Breaux et al. | 568/938 |
| 4,057,590 | 11/1977 | Gay | 568/938 |
| 4,138,438 | 2/1979 | Gay | 568/938 |
| 4,147,732 | 4/1979 | Mendiratta | 568/938 |

*Primary Examiner*—Leland A. Sebastian
*Attorney, Agent, or Firm*—Marvin Bressler

[57] ABSTRACT

Disclosed is a process for producing pentachloronitrobenzene (PCNB) by the reaction of pentachlorothiophenol with nitric acid in the presence of sulfuric acid or oleum.

14 Claims, No Drawings

PROCESS FOR PRODUCING PENTACHLORONITROBENZENE

BACKGROUND OF THE INVENTION

1. Field of the Invention

This invention relates to the production of pentachloronitrobenzene.

2. Brief Description of the Prior Art

Pentachloronitrobenzene (sometimes referred to herein as PCNB) is widely used today as a soil fungicide. It is particularly useful in controlling plant diseases caused by botrytis, fusarium, rhizoctonia and anthracnose.

Several methods are known for the preparation of PCNB. For example, U.S. Pat. No. 4,026,955, which issued on May 31, 1977 to Breaux, Newman and Quinnett, teaches one such process. That patent teaches reacting pentachlorobenzene and a mixed nitration acid in three stages having specific temperature requirements. U.S. Pat. No. 4,057,590, which issued on Nov. 8, 1977 to Gay, discloses a low temperature process for making PCNB by reacting pentachlorobenzene with substantially pure nitric acid. Also, U.S. Pat. No. 4,138,438, which issued on Feb. 6, 1979 to Gay, teaches another multi-step reaction between pentachlorobenzene and a mixed nitration acid and HCl. And U.S. Pat. No. 4,147,732, which issued on Apr. 3, 1979 to Mendiratta, discloses a process with a two-stage reactant mixing step wherein pentachlorobenzene is first mixed with sulfuric acid and then concentrated nitric acid is added.

While the processes disclosed by these four references represent significant advances in producing relatively high purity PCNB, there is still a need in the art to be able to produce high purity PCNB from precursors other than pentachlorobenzene, which is not always commercially available. The present invention covers such a process for making PCNB from a precursor that was unthought of for this use until the present invention.

BRIEF SUMMARY OF THE INVENTION

The present invention, therefore, is directed to a process for producing pentachloronitrobenzene comprising
reacting pentachlorothiophenol (PCTP) with a mixed nitration acid comprising nitric acid and sulfuric acid (and, preferably, sulfur trioxide to form oleum) at a temperature from about 35° to about 110° C. to form pentchloronitrobenzene, the nitric acid being in molar excess of the pentachlorothiophenol.

DETAILED DESCRIPTION

The exact mechanism by which PCTP reacts with nitric acid in the presence of $H_2SO_4$ or oleum to form PCNB is not known. It is believed that the PCTP reacts with $HNO_3$ in the presence of oleum by more than one reaction route. Two theorized routes are shown below by reaction equations (A) and (B):

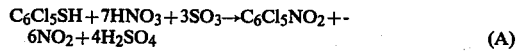
(A)

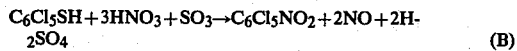
(B)

As can be seen, $NO_2$ or $NO$ is produced as a by-product of each route. Since mixtures of $NO_2$ and $NO$ may be in the resulting reaction mixture, it is believed that the formation of PCNB from PCTP occurs simultaneously by both reaction mechanisms (A) and (B) and possibly others. Of course, the present invention is not to be limited to any particular reaction mechanisms.

PCTP is a commercially known chemical which has been used as a masticating agent in the rubber industry. It is normally produced by reacting hexachlorobenzene [sometimes referred hereafter as (HEX)] with sodium sulfide or hydrosulfide. See U.S. Pat. No. 3,560,573, which issued on Feb. 2, 1971 to Blazejak and Haydn, and U.S. Pat. No. 3,474,139, which issued on Oct. 21, 1969 to Leib. Also see Japanese Pat. No. 81/04,547, which issued on Jan. 30, 1981 to the Sugai Chemical Industry Co., Ltd. Alternatively, the present invention covers alkali metal salts, especially the sodium salt, of PCTP as equivalents of PCTP itself.

An important advantage of this invention is that it allows the conversion of hexachlorobenzene, an unwanted by-product of conventional PCNB production methods, back to PCNB. By this recycle process, the undesirable HEX, is converted to PCTP, advantageously by reacting it with NaSH in the presence of a base such as NaOH or $Na_2CO_3$. Then, the PCTP is changed into PCNB by the reaction of the present invention. Thus, the unwanted and possibly harmful by-product HEX is converted into the useful PCNB.

The mixed nitration acid reactant is, as indicated above, comprised of sulfuric acid and nitric acid. It is preferred that sulfur trioxide also be present (as in commercial oleum). While it is not believed to be critical, it is advantageous to employ a weight ratio of sulfuric acid to nitric acid of at least about 0.1:1 in order to achieve desirable yields of PCNB. It is more preferred to employ a weight ratio of at least about 0.2:1, most preferably, from about 0.25:1 to about 1.1:1, of these two acids for optimum yields. Also, it is desirable to employ $SO_3$ in amounts from about 1% to about 30%, more preferably, at least about 10% by weight of the $H_2SO_4$ employed.

Sufficient mixed nitration acid should be employed so as to have a molar excess of $HNO_3$ over PCTP. As can be seen from equations (A) and (B), above, the theorized reaction mechanisms require this molar excess. Advantageously, the mole ratio is preferred to be at least about 3:1. More preferably, it is desirable to employ sufficient nitric acid so that the molar ratio is from about 10:1 to about 40:1.

Preferably, the nitric acid and sulfuric acid (oleum may be substituted for the latter) making up this mixed nitration acid are both in the most concentrated form as possible. Desirably, the nitric acid making up part of the mixed nitration acid is concentrated nitric acid having at least about 65%, more preferably at least about 90%, by weight of $HNO_3$. The sulfuric acid is preferably in concentrated form containing at least about 85%, more preferably 95%, by weight of $H_2SO_4$.

Sufficient sulfuric acid should preferably be present to act simultaneously as a solvent and catalyst and to absorb water formed during the reaction. In particular, regarding its catalytic effect, it is known that the presence of sulfuric acid protonates the nitric acid and, thus, makes the nitric acid a more reactive species for the present invention. The additional presence of $SO_3$ is preferred because it is believed that a higher yield and a purer product may occur.

The reaction of the present invention may be conducted by mixing together the PCTP and the mixed nitration acid in one or two stages. For example, one preferred embodiment is to mix the PCTP and concentrated nitric acid in one reaction vessel and then adding concentrated sulfuric acid (or oleum) to this mixture. In another preferred embodiment, the PCTP is added to a mixture of nitric acid and sulfuric acid (or oleum). Alternatively, the acid mixture may be added to the PCTP. However, the mode of addition is not a critical feature of this invention as long as desired reaction temperatures are maintained during the addition period.

The reaction between PCTP and the mixed nitration acid is highly exothermic. In order to control the temperature of the reaction mixture, it is preferred to add the PCTP to the acids, or vice versa, at a rate sufficient to control the temperature to within the desired temperature range. If external cooling is provided more rapid addition may be utilized, but such cooling is not essential. Also, it is preferred that the reaction mixture be well mixed by known stirring or agitation techniques to better ensure proper overall temperature control.

If the above-noted two stage mixing process is employed, the addition of the PCTP to the nitric acid, or vice versa, is preferred to be made at a rate sufficient to maintain the reaction mixture at a temperature from about 35° C. to about 65° C. At temperatures below about 35° C., several production problems may be encountered involving difficult temperature control and inadequate production rates. At an initial reaction temperature above about 65° C., the rate of by-product formations, including the forming of undesired hexachlorobenzene, may occur. Accordingly, it is preferred to conduct this first stage addition within the specified range, more preferably, from about 45° C. to about 60° C. In the second stage, the sulfuric acid or oleum is added to this resulting mixture at a rate sufficient to keep the reaction mixture from about 55° C. to about 100° C. Temperatures below about 55° C. for this stage are not preferred because the reaction rates would be too slow for most commercial modes. Likewise, allowing the reaction temperature to rise above about 100° C. may result in the formation of undesirable impurities like hexachlorobenzene. More preferably, it is desired that this second stage be carried out at temperatures from about 60° C. to about 85° C.

If the above-noted one stage mixing process is employed, the addition of the PCTP to the mixed acids, or vice versa, is preferably carried out from about 55° C. to about 100° C. for the same reasons as stated above. More preferably, the reaction is conducted in a range from about 60° C. to about 85° C. for this single stage.

Regardless of whether one or two-stage mixing steps, or other mixing procedures are followed, the reaction mixture should be maintained at the above-noted temperature range(s) for a sufficient amount of time to convert at least a portion of the PCTP to PCNB. Preferably, the amount of time should be sufficient to convert substantially all (i.e. greater than 95% by weight) of the PCTP. In order to achieve this desired conversion, it is preferred to allow the reaction mixture to react from about 15 minutes to about 180 minutes, or greater. Of course, the reaction time will depend upon the specific reaction temperatures employed and the mole and weight ratios of $HNO_3$:PCTP and $HNO_3$:$H_2SO_4$ employed, respectively. To minimize the time period of the reaction, it is preferable to utilize a combination of reaction temperature(s) and mole and weight ratios which results in the substantial complete conversion of PCTP while minimizing the amount of by-products produced.

After the reaction has achieved its desired completion, the solid PCNB crystals formed may be recovered or subjected to further chemical reaction in the production of other chemicals. Product recovery can be achieved by any suitable technique such as any conventional liquid/solid separation means such as filtration, centrifugation, decanting and the like. Preferably, the temperature of the reaction mixture, after completion of the reaction, is cooled to a temperature from about 0° C. to about 30° C. and then the PCNB is separated from the reaction mixture. The preferred separation means is filtration. This may also be followed by washing with water or any other suitable solvent to remove residuals. Alternatively, a hot filtration without cooling may be preferred in some instances. A highly pure PCNB product may be made according to this invention with the levels of hexachlorobenzene preferably being less than 1.0% by weight of the total PCNB product.

The process of this invention was totally unexpected and surprising because there is no open position on the PCTP molecule for substitution with a nitro group. One woud believe that the —SH and —Cl groups would not be readily reactive for substitution. But, if so, a wide variety of co-products would be produced. In the prior art methods of making PCNB, the pentachlorobenzene precursor has one open position on the ring free for substitution with a nitro group. That is not the case here. Furthermore, one might expect that the reaction of the $HNO_3$ with the —SH group on the PCTP compound would form other substituents, such as "sulfonic acid group."

The following examples further illustrate the present invention. All parts and percentages are by weight unless otherwise expressly indicated.

EXAMPLE 1

PCNB from Pentachlorothiophenol Using 70% Nitric Acid and 30% Oleum

Pentachlorothiophenol (10.0 g, 0.035 mol) was added to 60.0 g of 70% nitric acid at room temperature. The reaction mixture was heated at reflux 7 hr followed by stirring at room temperature 16 hr. At this point, 40 mL of 30% oleum (30% by weight sulfur trioxide in sulfuric acid) was added at such a rate that the temperature was maintained between 55° and 60° C. After the addition was complete (30 min), the reaction mixture was heated at 108° C. for 30 minutes. The reaction mixture was then cooled to room temperature, filtered, the product washed with water and dried in vacuo to give 7.6 g (74% yield) of 99.0% PCNB with 1.0% hexachlorobenzene (GC assay).

EXAMPLE 2A

PCNB from Pentachlorothiophenol Using 99% Nitric Acid and 30% Oleum in a One-pot, Two-step Process Pentachlorothiophenol (10.0 g, 0.035 mol) was added to 60.0 g of 99% nitric acid over 20 min at 45°–50° C. followed by heating at reflux (55° C.) for 1.5 hr. At this point 20 mL of 30% by weight oleum was added at such a rate that the temperature was kept at 75° to 80° C. After the addition was complete (approximately 30 min.), the reaction mixture was cooled to room temperature. The product was collected by filtration, and thoroughly washed with water to give after drying in vacuo, 8.6 g (85% yield) of 99.7% PCNB with 0.17% hexachlorobenzene (GC assay). Variations on this one-pot, two-step process were examined and are summarized in TABLE I.

TABLE I

ONE-POT, TWO-STEP PCTP TO PCNB PROCESS[a]

| EXAMPLE | PCTP (g) | 99% HNO$_3$ (g) | PCTP ADD'N TIME (min)/TEMP (°C.) | REFLUX TIME (min) | 30% OLEUM mL (g) | YIELD (%) | PRODUCT ASSAY (%)[b] PCNB | HEX |
|---|---|---|---|---|---|---|---|---|
| 2B | 10 | 75 | 30 min (50–60° C.) | 30 | 10(18.8) | 82 | 99.6[c] | 0.08 |
| 2C | 10 | 45 | 30 min (50–60° C.) | 30 | 10(18.8) | 84 | 99.3 | 0.2 |
| 2D | 10 | 30 | 30 min (50–60° C.) | 30 | 10(18.8) | 19 | 99.1 | 0.2 |
| 2A | 10 | 60 | 20 min (45–50° C.) | 90 | 20(37.6) | 85 | 99.7 | 0.17 |
| 2E | 25 | 150 | 40 min (50–60° C.) | 30 | 30(56.6) | 81 | >99.5 | <0.2 |
| 2F | 25 | 150 | 40 min (50–60° C.) | 30 | 25(47.0) | 82 | 99.6 | 0.07 |
| 2G | 25 | 150 | 40 min (50–60° C.) | 30 | 15(28.2) | 53 | >99.5 | <0.02 |
| 2H | 25 | 150 | 40 min (50–60° C.) | 30 | 10(18.8) | 10 | >99.5 | <0.2 |

[a]Procedure and work-up outlined in Example 2A
[b]Measured by GC internal area normalization assay.
[c]Elemental analysis. Calc'd for C$_6$Cl$_5$NO$_2$: C, 24.40; Cl, 60.02; N, 4.74. Found: C, 24.18; Cl, 59.68; N, 4.84.

EXAMPLE 3A

PCNB from Pentachlorothiophenol Using 99% Nitric Acid and 30% Oleum in a One-pot, One-step Process A 10 mL aliquot of 30% oleum was added to 60.0 g 99% nitric acid resulting in a temperature rise to 65° C. Pentachlorothiophenol (10.0 g, 0.035 mol) was added at such a rate that the temperature was maintained between 65° C. and 70° C., with a total addition time of 1.0 hr. The reaction mixture was cooled to room temperature, and the product collected by filtration, followed by a thorough water wash and drying in vacuo. The product, 8.5 g (82% yield), analyzed (GC) as 98.6% PCNB with 0.09% hexachlorobenzene. Variations on this one-pot, one-step process are summarized in TABLE II.

TABLE II

ONE-POT, ONE-STEP PCTP TO PCNB PROCESS[a]

| EXAMPLE | PCTP (g) | HNO$_3$ (g) | 30% OLEUM mL (g) | PCTP ADD'N TIME (min) | YIELD (%) | PRODUCT ASSAY (%)[b] PCNB | HEX |
|---|---|---|---|---|---|---|---|
| 3A | 10 | 60 | 10(18.8) | 60 | 82 | 98.6 | 0.09 |
| 3B | 25 | 113 | 25(47) | 80 | 83 | 97.5 | 0.10 |
| 3C | 25 | 75 | 25(47) | 80 | 74 | 97.3 | 0.09 |
| 3D | 25 | 75 | 25(47) | 80[c] | 72 | not determined | not determined |

[a]Procedure and work-up outlined in Example 3A.
[b]Measured by GC internal area normalization assay.
[c]The addition of PCTP was followed by a 60 min heating step at 70° C.

EXAMPLE 4

PCNB from Pentachlorothiophenol Using 99% Nitric Acid and Concentrated Sulfuric Acid Pentachlorothiophenol (10.0 g, 0.035 mol) was added to 60.0 g 99% nitric acid over 0.5 hr followed by a 0.5 hr reflux at 55° C. At this point, 10 mL of concentrated sulfuric acid was added over a 10 min period, and the reaction mixture heated at 65°–70° C. for 15 min. The reaction mixture was cooled to room temperature, the product collected by filtration, and thoroughly washed with water giving after drying in vacuo 6.5 g (62% yield) of 98.6% PCNB with 0.54% hexachlorobenzene (GC assay).

EXAMPLE 5

PCNB from Sodium Pentachlorothiophenolate

The sodium salt of pentachlorothiophenol was prepared by heating at 80° C. for 3 hr a reaction mixture consisting of 25.0 g (0.088 mol) hexachlorobenzene and 15 g (0.195 mol) sodium sulfhydrate (73% assay) in 100 mL DMF. The solvent was removed by distillation in vacuo and the resulting residue (36.3 g) added to a solution of 45 g of 30% oleum in 150 g of 99% nitric acid which was preheated to 65° C. The addition was made in 0.5 hr while the reaction temperature was maintained at 60°–65° C. by ice-bath cooling. The reaction mixture was cooled to room temperature, filtered, and the residue washed into water. After drying in vacuo 21.3 g of product was obtained which assayed (GC) at 97% PCNB, 0.26% hexachlorobenzene.

We claim:

1. A process for producing pentachloronitrobenzene comprising:
reacting pentachlorothiophenol with a mixed nitration acid comprising nitric and sulfuric acid at a temperature from about about 35° C. to 110° C. to form pentachloronitrobenzene, said nitric acid being in molar excess of said pentachlorothiophenol.

2. The process of claim 1 wherein said mixed nitration acid further comprises sulfur trioxide.

3. A process for producing pentachloronitrobenzene comprising:
(a) mixing pentachlorothiophenol with nitric acid at a temperature from about 35° C. to about 65° C., said nitric acid being in molar excess of said pentachlorothiophenol;
(b) mixing the resulting mixture with sulfuric acid at a temperature from about 55° C. to about 100° C., the weight ratio of said sulfuric acid to said nitric acid being at least 1.1:1, and (c) maintaining said reaction mixture within said temperature range for sufficient time to convert at least a portion of said pentachlorothiophenol to pentachloronitrobenzene.

4. The process of claim 3 wherein sulfur trioxide is added with said sulfuric acid in step (b).

5. The process of claim 4 wherein the molar ratio of said nitric acid to said pentachlorothiophenol is at least 3:1.

6. The process of claim 5 wherein said mixing step (a) is carried out from about 45° C. to about 60° C.

7. The process of claim 6 wherein said mixing step (b) is carried out at a temperature from about 60° C. to about 85° C.

8. The process of claim 7 wherein said weight ratio of said sulfuric acid to said nitric acid is at least about 0.2:1.

9. The process of claim 8 wherein the amount of sulfur trioxide is from about 1% to about 30% by weight of the sulfuric acid present.

10. A process for producing pentachloronitrobenzene comprising:

(a) mixing pentachlorothiophenol with a mixed nitration acid comprising sulfuric acid and nitric acid at a temperature from about 55° C. to about 100° C., said nitric acid being in molar excess of said pentachlorothiophenol and the weight ratio of said sulfuric acid to said nitric acid being at least 0.1:1; and (b) maintaining said reaction mixture within said temperature range for sufficient time to convert at least a portion of said pentachlorothiophenol to pentachloronitrobenzene.

11. The process of claim 10 wherein said mixed nitration acid further comprises sulfur trioxide.

12. The process of claim 11 wherein the molar ratio of said nitric acid to said pentachlorothiophenol is at least 3:1.

13. The process of claim 12 wherein said weight ratio of said sulfuric acid to said nitric acid is at least about 0.2:1.

14. The process of claim 13 wherein the amount of sulfur trioxide is from about 1% to about 30% by weight of the sulfuric acid present.

* * * * *